(12) United States Patent
Palley et al.

(10) Patent No.: US 11,039,788 B2
(45) Date of Patent: Jun. 22, 2021

(54) WEARABLE FORCE SENSOR FOR MONITORING RESPIRATION

(71) Applicant: Spire, Inc., San Francisco, CA (US)

(72) Inventors: Jonathan Paul K. Palley, Fair Oaks, CA (US); Zhao Zhao, Beijing (CN)

(73) Assignee: Spire, Inc., San Francisco, CA (US)

( * ) Notice: Subject to any disclaimer, the term of this patent is extended or adjusted under 35 U.S.C. 154(b) by 0 days.

(21) Appl. No.: 16/271,492

(22) Filed: Feb. 8, 2019

(65) Prior Publication Data

US 2019/0223799 A1    Jul. 25, 2019

Related U.S. Application Data

(63) Continuation of application No. 14/174,466, filed on Feb. 6, 2014, now abandoned.
(Continued)

(51) Int. Cl.
*A61B 5/08* (2006.01)
*A61B 5/00* (2006.01)
(Continued)

(52) U.S. Cl.
CPC .......... *A61B 5/6823* (2013.01); *A61B 5/0816* (2013.01); *A61B 5/1118* (2013.01);
(Continued)

(58) Field of Classification Search
CPC ... A61B 5/6823; A61B 5/1118; A61B 5/0816; A61B 5/0402; A61B 5/1135;
(Continued)

(56) References Cited

U.S. PATENT DOCUMENTS

| 4,381,788 A | * | 5/1983 | Douglas | A61B 5/6892 |
| | | | | 361/283.1 |
| 4,813,428 A | | 3/1989 | Muraki | |

(Continued)

FOREIGN PATENT DOCUMENTS

| CN | 101917903 | 12/2010 |
| EP | 0699052 | 3/1996 |

OTHER PUBLICATIONS

International Preliminary Report on Patentability issued in PCT/US2014/015098 dated Aug. 11, 2015 in 6 pages.
(Continued)

*Primary Examiner* — Christian Jang
(74) *Attorney, Agent, or Firm* — Knobbe, Martens, Olson & Bear LLP (57) ABSTRACT

A system and method for monitoring respiration of a user, comprising: a respiration sensing module including a sensor configured to detect a set of respiration signals of the user based upon movement resulting from the user's respiration; a supplementary sensing module comprising an accelerometer and configured to detect a set of supplemental signals from the user; an electronics subsystem comprising a power module configured to power the system and a signal processing module configured to condition the set of respiration signals and the set of supplemental signals; a housing configured to facilitate coupling of the respiration sensing module and the supplementary sensing module to the user; and a data link coupled to the electronics subsystem through the housing and configured to transmit data generated from the set of respiration signals and the set of supplemental signals, thereby facilitating monitoring of the user's respiration.

21 Claims, 7 Drawing Sheets

Related U.S. Application Data (60) Provisional application No. 61/762,875, filed on Feb. 9, 2013, provisional application No. 61/873,698, filed on Sep. 4, 2013.

(51) Int. Cl.
| | |
|---|---|
| *A61B 5/1455* | (2006.01) |
| *A61B 5/113* | (2006.01) |
| *A61B 5/11* | (2006.01) |
| *A61B 5/318* | (2021.01) |
| *A61B 5/0205* | (2006.01) |
| *A61B 5/085* | (2006.01) |
| *A61B 5/087* | (2006.01) |
| *A61B 5/024* | (2006.01) |

(52) U.S. Cl.
CPC ........ *A61B 5/1135* (2013.01); *A61B 5/14551* (2013.01); *A61B 5/318* (2021.01); *A61B 5/0205* (2013.01); *A61B 5/02416* (2013.01); *A61B 5/085* (2013.01); *A61B 5/087* (2013.01); *A61B 5/1112* (2013.01); *A61B 5/7282* (2013.01); *A61B 2562/0261* (2013.01)

(58) Field of Classification Search
CPC ........ A61B 5/14551; A61B 2562/0261; A61B 5/085; A61B 5/087; A61B 5/02416; A61B 5/1112; A61B 5/0205; A61B 5/7282
See application file for complete search history.

(56) References Cited

U.S. PATENT DOCUMENTS

| | | | |
|---|---|---|---|
| 5,611,349 A | 3/1997 | Halleck | |
| 6,480,111 B2 | 11/2002 | Canady | |
| 6,936,011 B2 | 8/2005 | Sheldon | |
| 8,140,154 B2 | 3/2012 | Donnelly | |
| 8,475,371 B2 | 7/2013 | Derchak | |
| 8,764,651 B2 | 7/2014 | Bao | |
| 9,545,222 B2 | 1/2017 | Derchak | |
| 9,699,528 B2 | 7/2017 | Rohan | |
| 2004/0077934 A1* | 4/2004 | Massad | A61B 5/0205 |
| | | | 600/300 |
| 2005/0245839 A1* | 11/2005 | Stivoric | A61B 5/6804 |
| | | | 600/549 |
| 2006/0122528 A1 | 6/2006 | Gal | |
| 2007/0027389 A1* | 2/2007 | Wesse | A61B 6/032 |
| | | | 600/407 |
| 2008/0082018 A1* | 4/2008 | Sackner | A61B 5/0476 |
| | | | 600/538 |
| 2008/0108903 A1 | 5/2008 | Ben-Oved | |
| 2009/0203972 A1 | 8/2009 | Heneghan | |
| 2010/0006106 A1 | 1/2010 | Balakin | |
| 2010/0201524 A1 | 8/2010 | Gallagher | |
| 2010/0328075 A1* | 12/2010 | Rahamim | A61B 5/1135 |
| | | | 340/573.1 |
| 2011/0066037 A1 | 3/2011 | Banet | |
| 2011/0066038 A1 | 3/2011 | Banet | |
| 2011/0130643 A1* | 6/2011 | Derchak | A61B 5/6805 |
| | | | 600/409 |
| 2011/0213271 A1 | 9/2011 | Telfort | |
| 2012/0041279 A1 | 2/2012 | Freeman | |
| 2012/0220835 A1 | 8/2012 | Chung | |
| 2012/0220888 A1* | 8/2012 | Wolfe | A61B 7/003 |
| | | | 600/534 |
| 2013/0066168 A1 | 3/2013 | Yang | |
| 2013/0085538 A1 | 4/2013 | Volpe | |
| 2014/0358012 A1 | 12/2014 | Richards | |
| 2016/0150982 A1 | 6/2016 | Roy | |
| 2016/0192856 A1 | 7/2016 | Lee | |
| 2016/0317089 A1 | 11/2016 | Fyfe | |
| 2016/0336501 A1 | 11/2016 | Kasichainula | |
| 2016/0346584 A1 | 12/2016 | Schneider | |
| 2017/0325525 A1 | 11/2017 | Hyde | |
| 2018/0008195 A1 | 1/2018 | Vaitaitis | |
| 2018/0108903 A1 | 4/2018 | Takeda et al. | |

OTHER PUBLICATIONS

International Search Report issued in PCT/US2014/015098 dated Apr. 16, 2014 in 2 pages.
Extended European Search Report issued in EP 14748473.7 dated Dec. 1, 2016 in 8 pages.
International Search Report issued in PCT/US2018/017275 dated Apr. 23, 2018.
International Preliminary Report on Patentability issued in PCT/2018/017275 dated Aug. 13, 2019.

* cited by examiner

WEARABLE FORCE SENSOR FOR MONITORING RESPIRATION

CROSS-REFERENCE TO RELATED APPLICATIONS

This application is a continuation of U.S. patent application Ser. No. 14/174,466, filed Feb. 6, 2014, which claims the benefit of U.S. Provisional Application Ser. No. 61/762,875, filed Feb. 9, 2013 and U.S. Provisional Application Ser. No. 61/873,698 filed Sep. 4, 2013, the entire disclosure of each of which is incorporated by reference in its entirety

TECHNICAL FIELD

This invention relates generally to the biosignal monitoring device field, and more specifically to a new and useful system and method for monitoring respiration.

BACKGROUND

Respiration parameters can provide profound insight into an individual's wellbeing. Respiration parameters can be indicative of physiological and/or mental states of an individual, as well as prognostic with regard to diagnosis of medical conditions. In examples, respiration parameters can provide insight into an individual's stress levels, and can be evidential of more serious pulmonary disorders, such as disorders associated with chronic obstructive pulmonary disease (COPD). Traditionally, however, respiration monitoring has occurred in a clinical setting, contributing to the developing of respiration monitoring devices that are motion-limiting, lack portability, and/or are difficult to use. There is thus a need in the biosignal monitoring device field to create a new and useful system for monitoring respiration. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

I. System

Figure 1:
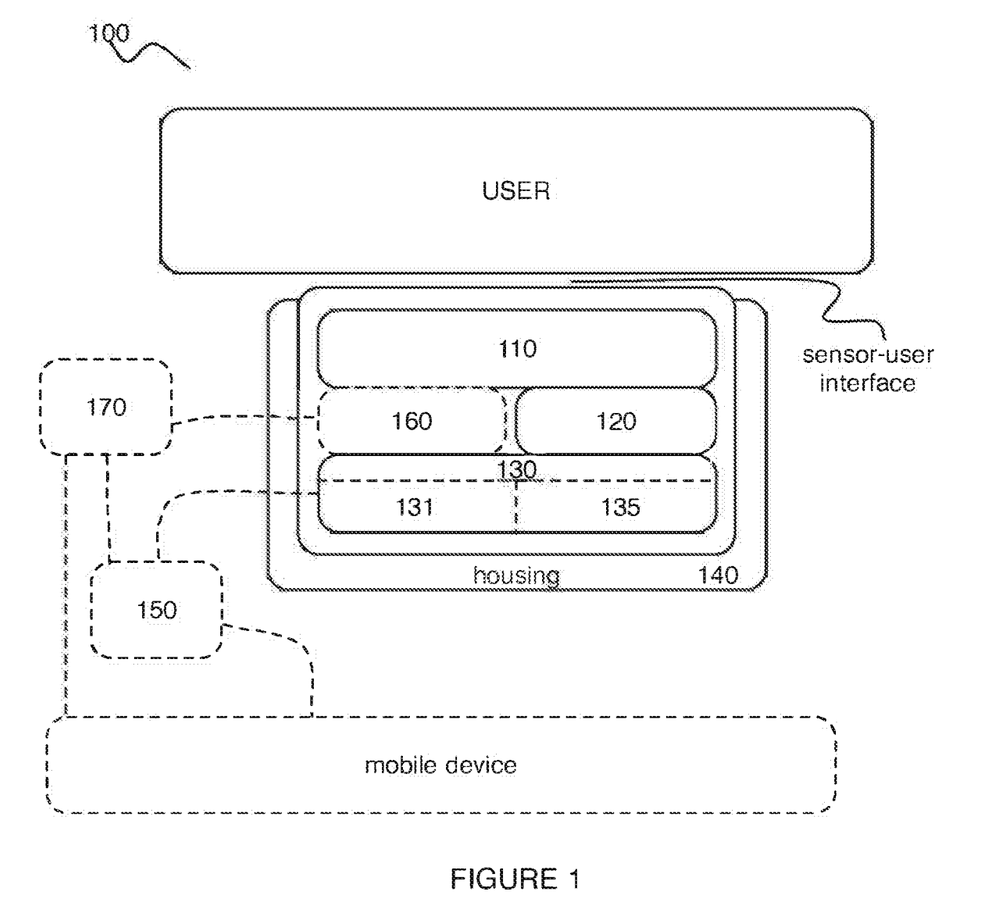
FIG. 1 depicts an embodiment of a system for monitoring respiration of a user.

As shown in FIG. 1, an embodiment of a system 100 for monitoring respiration of a user comprises: a respiration sensing module 110 comprising a sensor configured to detect a set of signals indicative of a set of respiration characteristics of the user (i.e., respiration signals); a supplementary sensing module 120 configured to detect a supplemental set of signals from the user; an electronics subsystem 130 comprising a power module and a signal processing module, and configured to process signals of the set of signals and the supplemental set of signals; and a housing 140 configured to house elements of the system 100. Embodiments of the system 100 can further comprise a data storage unit 150 coupled to the electronics subsystem 130 and configured to store data relevant to the respiration characteristics of the user; a data link 160 coupled to the electronics subsystem 130 and configured to provide and/or receive data relevant to the set of respiration characteristics of the user; a processor 170 coupled to at least one of the data storage unit 150 and the data link 160 and configured to generate an analysis based upon the set of respiration characteristics of the user; and a user interface configured to inform the user based upon the analysis.

The system 100 functions to detect signals indicative of a user's respiration characteristics and to provide data relevant to the user's respiration characteristics for further analysis, such that the user's respiration behavior can be effectively monitored. The system 100 is also preferably configured to provide information regarding the user's respiration characteristics to the user and/or other entity at a user interface. Analyses generated based upon the user's respiration characteristics can thus be used to inform the user of his/her respiration behavior, and can additionally lead to a change in the user's respiration behavior based upon the analyses provided to the user and/or other entity. Preferably, the user's respiration characteristics are monitored by the system 100 substantially continuously and in real time; however, the user's respiration characteristics can alternatively be monitored intermittently and/or in non-real time.

The system 100 can function to monitor and/or indicate physiological and/or mental states of the user based upon the user's respiration characteristics, and can additionally or alternatively function to facilitate diagnosis of medical conditions with pulmonary indications. In examples, the system 100 can facilitate monitoring and/or indication of a user's stress levels and physical exertion (e.g., during exercise) based upon respiration characteristics. In other examples, the system 100 can function to indicate signs of medical conditions, such as conditions associated with COPD (e.g., apnea, asthma, emphysema). In one such example, the system 100 can indicate a breathing abnormality of the user, which can be used to initiate diagnosis of a condition of the user's upper respiratory tract, trachea, bronchi, bronchioles, alveoli, pleura, pleural cavity, and/or any nerves or muscles associated with breathing. The system 100 can, however, be configured to monitor any other suitable respiration behavior of a user, and/or indicate any other suitable sign of a respiration-related medical condition.

Preferably, the system 100 is configured to be worn by the user outside of a clinical (e.g., hospital) or research (e.g., laboratory) setting, such that the user can be in a non-contrived environment as he or she is undergoing respiration monitoring. Additionally, the system 100 preferably does not inhibit mobility of the user, such that respiration monitoring can occur as the user performs normal activities (e.g., walking, exercising, working, etc.) in his/her daily life. Furthermore, elements of the system 100 can be reusable or disposable, or the entire system 100 can be configured to be disposable. In one specific example, the system 100 is a unitized system 100 that couples to the user (e.g., to the user's skin, to the user's clothing), thus not compelling the patient to hold any part of the system 100 by hand; however, in the specific example, the housing 140 is configured to reversibly couple and uncouple from other system elements, in order to provide modularity and versatility in coupling to a user. Furthermore, the system 100 is preferably configured to monitor the user's respiration non-invasively and in a manner wherein the user is substantially removed from clinical/research staff. Alternatively, the system 100 can be substantially non-portable, non-wearable, and/or intended for use in a clinical or research setting.

1.1 Sensing Modules

The respiration sensing module 110 comprises a sensor configured to detect a set of signals indicative of a set of respiration characteristics (i.e., respiration signals) of the user, and functions to sense movement of a portion of the user's body, wherein the movement results from the user's respiration. The respiration sensing module 110 is preferably coupled directly to the user (e.g., to the user's clothing, to the user's skin) in a manner that provides robust contact between the user and the respiration sensing module at a sensor-user interface. After coupling, the sensor-user interface is preferably substantially fixed, such that motion detection associated with breathing can be easily distinguished from any other motion (e.g., gross motions of the user). The sensor-user interface is preferably located proximal to the user's torso (e.g., abdomen region, hip region, chest region). Furthermore, the sensor-user interface is preferably defined as a region displaced in a superficial direction (e.g., along a superficial-deep axis through the torso of the user); however, the sensor-user interface can alternatively be defined in any other suitable manner. The sensor-user interface can be a substantially single point of contact on the user, can be defined as a planar surface between a surface of a sensor of the respiration sensing module and a surface of the user's body, and/or can be defined as a volume between a surface of a sensor of the respiration sensing module and an opposing surface of the user's body. However, the sensor-user interface can be located at any suitable location relative to the user and can be defined relative to the user in any other suitable manner. Alternatively, the sensor user interface can be non-fixed, and the system 100 can be configured to distinguish motion of the user's body associated with breathing from other detected motions (e.g., motion of the sensor relative to the user's body, gross motions of the user).

Preferably, the sensor of the respiration sensing module 110 functions based upon respiratory inductance plethysmography (RIP), and preferably functions to detect motions of the user's chest and/or abdominal wall produced during the user's breathing. Additionally, the respiration sensing module 110 is preferably non-invasive in detecting signals indicative of the user's respiration behavior; however, the respiration sensing module 110 can comprise invasive or minimally invasive elements. Alternatively, the respiration sensing module 110 can function based upon any other suitable plethysmography-based sensing method, any other suitable mechanical sensing method (e.g., acoustic sensing), and/or any suitable sensing method (e.g., ultrasound respiration sensing). Additionally, the respiration sensing module 110 preferably detects signals indicative of the user's respiration characteristics substantially continuously and in real time; however, the respiration sensing module 110 can alternatively or additionally detect signals intermittently and/or not in real time.

In a first variation, the respiration sensing module 110 preferably comprises a sensor including at least one element configured to deflect in response to movements of the user's body produced by the user's breathing, or to detect force in response to the user's breathing in any other suitable manner (e.g., without deflection of an element). In the first variation, forces generated during the user's respiration, in a direction perpendicular to a surface of the respiration sensing module 110 (i.e., at the sensor-user interface), are preferably detected by the sensor and used to determine characteristics of the user's respiration. As such, forces perpendicular to the sensor-user interface (e.g., along a superficial-deep direction) and perpendicular to a surface of the user's body can be used to determine aspects of the user's respiration. For example, the respiration sensing module does not require coupling to the user by way of an element that wraps about the user's torso and transmits tangential forces to the respiration sensing module 110 during the user's respiration. However, tangential forces generated at the respiration sensing module 110 during the user's respiration can additionally or alternatively be used to determine characteristics of the user's respiration.

The element of the sensor is preferably configured to directly or indirectly (e.g., by way of a housing) provide a robust connection with the user, such that deflections associated with the user's breathing are detected with minimal interference due to other motions of the user and/or sensor. In the first variation, the respiration sensing module can include a sensing element (e.g., the sensor) that is constrained at opposing sides, in order to enhance an effect of respiration-induced motion of the user's body (e.g., abdominal region, chest region). In one example, the respiration sensing module can thus be positioned between the user's clothing and the user's skin, coupled robustly to an article of the user's clothing, and/or coupled to the user using any one or more of an adhesive (e.g., permanent adhesive, non-permanent adhesive), strap, clip, or other suitable coupling element. In alternative configurations, the sensing element of the respiration sensing module can be constrained at any other suitable number of sides and in any other suitable configuration, such that the user's respiration can be sensed at the sensing element.

In a first example of the first variation, the sensor comprises a force-sensing resistor configured to generate a response in resistance upon being subject to an applied force. In the first example, the force sensing resistor is configured to provide a response in resistance (e.g., decrease in resistance) with an increase in applied force (e.g., when the resistor is placed under compression). In a variation of the first example, the force sensing resistor is configured to provide a response in resistance (e.g., a decrease in resistance) with a decrease in applied force (e.g., when the resistor is placed under tension). However, in variations of the first example, the force sensing resistor can additionally or alternatively be configured to provide any suitable change decrease in applied force (e.g., when the resistor is placed under tension). In the first example, the force-sensing resistor includes a conductive polymer film (e.g., polymer thick film) including electrically conducting and non-conducting particles suspended in matrix, coupled to a set of electrodes. Upon application of a force to the matrix, conducting particles are moved in proximity and/or into contact with the set of electrodes, adjusting a resistance of the film in response to the applied force. In the first example, the force-sensing resistor can be positioned between the user's clothing and the user's body (e.g., at an abdomen region, at a chest region, between an undergarment and the user's body, etc.) and configured such that application of a force to the resistor, in a direction perpendicular to the surface of the user's body at the sensor-user interface, is detected and produces a change in resistance. As such, the respiration sensing module 110 is able to produce electrical signals (e.g., resistance changes) m response to compression/decompression of the sensor resulting from the user's breathing. In variations of the first example, the sensor can include multiple force-sensing resistors and/or other sensing elements, which can facilitate determination of additional aspects of an applied force (e.g., centroid of force, etc.), for example, in applications involving placement guidance for the respiration sensing module 110.

In a second example of the first variation, the sensor comprises a capacitor that is configured to produce an electrical signal (e.g., change in electric field) in response to a deflection of a first capacitor plate relative to a second capacitor plate. The first and the second plates of the capacitor are separated in the second example by a non-rigid material that provides support to each plate of the capacitor. In the second example, the first and the second plates of the capacitor are preferably oriented with faces parallel to the surface of the user at the sensor-user interface, such that deflections perpendicular to the faces of the capacitor plates, produced by breathing, are detected by the respiration sensing module. As such, the capacitor plates can be positioned between the user's clothing and the user's body (e.g., at an abdomen region, at a chest region, between an undergarment and the user's body, etc.) and configured such that deflections of one capacitor plate relative to another capacitor plate, with deflection components perpendicular to the surface of the user's body at the sensor-user interface, are detected. As such, the respiration sensing module 110 is able to produce electrical signals in response to compression/decompression of the sensor resulting from the user's breathing. In a variation of the second example, the capacitor can be a fluid capacitor coupled to a pressure sensor, such that deflection/deformation of the fluid capacitor produces a detectable change in pressure at the pressure sensor, which results in a detected electrical signal indicative of the user's respiration. In variations of the second example, the sensor can include multiple capacitive elements and/or other sensing elements, which can facilitate determination of additional aspects of an applied force (e.g., centroid of force, etc.), for example, in applications involving placement guidance for the respiration sensing module 110.

Figure 2A:
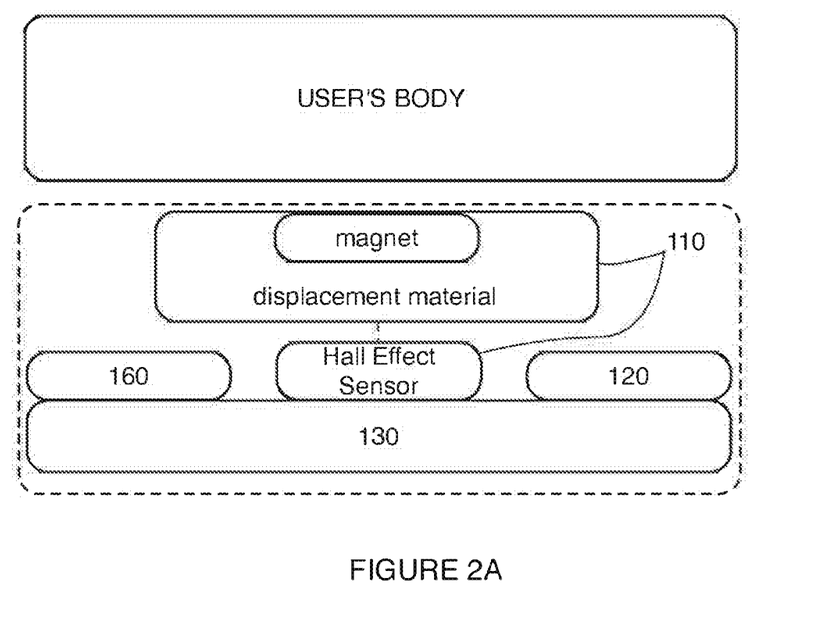
FIGS. 2A and 2B depict examples of a portion of a system for monitoring respiration of a user.

In a third example of the first variation, as shown in FIG. 2A, the sensor comprises a magnetic element and a hall-effect sensor, wherein a change in magnetic field, produced by deflection of the magnetic element, is detected by the hall-effect sensor and produces an electrical signal indicative of the user's respiration. In the third example, the magnetic element is separated from the hall-effect sensor by a nonrigid material or structure, which can include a spring-loaded platform or elastomeric material (e.g., silicon-based material) to which the magnetic element is coupled (e.g., embedded, attached, etc.). In the third example, the magnetic element and the hall-effect sensor are positioned between the user's clothing and the user's body (e.g., at an abdomen region, at a chest region, between an undergarment and the user's body, etc.) and configured such that deflections of the magnetic element relative to the hall-effect sensor, with deflection components perpendicular to the surface of the user's body at the sensor-user interface, are detected. As such, the respiration sensing module 110 is able to produce electrical signals in response to compression/decompression of the sensor resulting from the user's breathing. In variations of the third example, the sensor can include multiple hall-effect sensors and/or other sensing elements, which can facilitate determination of additional aspects of an applied force (e.g., centroid of force, etc.), for example, in applications involving placement guidance for the respiration sensing module 110.

Figure 2B:
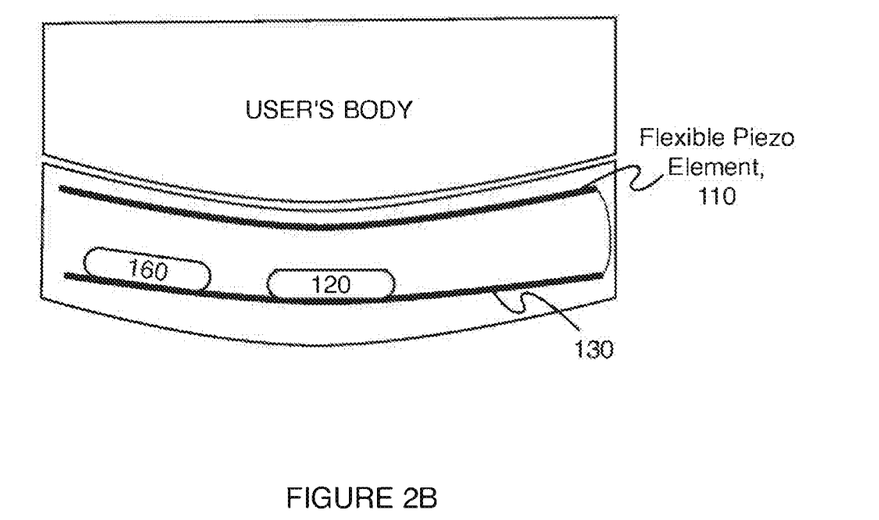

In a fourth example of the first variation, as shown in FIG. 2B, the sensor is a piezoelectric sensor that produces an electrical signal in response to deformation of a piezoelectric material of the sensor. The piezoelectric sensor in the fourth example can be flexible and embedded in an article of the user's clothing (e.g., bra, waistband, belt) or positioned between the user's body and an article of clothing, such that motion of the user, produced by respiration, deforms the piezoelectric material and produces an electrical signal indicative of the user's respiration. In the fourth example, the piezoelectric sensor is thin and characterized by a low-aspect ratio, as shown in FIG. 2B, in order to facilitate deformation of the piezoelectric material to provide greater sensitivity. In other variations of the fourth example, the piezoelectric sensor can be characterized by any suitable morphology and/or profile. In variations of the fourth example, the sensor can include multiple piezoelectric elements and/or other sensing elements, which can facilitate determination of additional aspects of an applied force (e.g., centroid of force, etc.), for example, in applications involving placement guidance for the respiration sensing module 110.

In another variation, the respiration sensing module 110 can additionally or alternatively comprise a mechanical sensing element, which mechanically detects the user's respiration. In an example, the respiration sensing module 110 can comprise an acoustic sensor (e.g., microphone) configured to detect acoustic signals indicative of the user's respiration. In another example, the respiration sensing module 110 can comprise a mechanical deformation sensor (e.g., strain gage) configured to deform to mechanically detect the user's respiration. Other examples can comprise any other suitable sensor configured to mechanically detect signals indicative of the user's respiration.

In yet another variation, the respiration sensing module 110 can additionally or alternatively comprise an ultrasound transducer (e.g., ultrasound proximity sensor) configured to ultrasonically detect signals indicative of the user's respiration. The ultrasound transducer can comprise a set of ultrasound emitters configured to emit acoustic signals toward the user and a set of ultrasound receivers configured to receive acoustic signals from the user, wherein the received signals are indicative of motions of the user's abdomen and/or chest produced during breathing. The respiration sensing module 110 can, however, comprise any suitable combination of any of the above variations and examples, and/or combinations of any variation or example with any other suitable respiration sensing module. For example, the respiration sensing module 110 can comprise multiple sensor types and/or multiples of a single sensor type to provide redundancy in means for respiration signal detection.

The set of respiration characteristics characterized in the set of respiration signals preferably comprises any one or more of: respiration rate (e.g., breaths per second), depth of breath, shallowness of breath, inhalation-to-exhalation ratio, thoracic variations, tidal volume (or an estimation thereof), inspiratory flow (e.g., peak value, mean value), expiratory flow (e.g., peak value, mean value), fractional inspiratory time, work of breathing, phase angle, respiration waveform morphology (e.g., shape, area under waveform, regularity of waveform, etc.), any other suitable respiration characteristic, and any other suitable derivative of a respiration characteristic. With regard to respiration waveform morphology, respiration characteristics can include, for example, a sharpness of a transition between inhalation and exhalation for a user, as indicated by the respiration waveform, a length of breath holding by the user, as indicated by the respiration waveform, or any other suitable factor. Additionally, the set of respiration characteristics can indicate respiration events associated with laughter, sighing, wheezing, coughing, apnea, and/or any other suitable event associated with the user's respiration.

The supplementary sensing module 120 is configured to detect a supplemental set of signals from the user, and functions to provide additional data that facilitates processing of the set of signals indicative of the set of respiration characteristics. As such, the supplementary sensing module 120 can enable extraction of a set of respiration characteristics from the set of respiration signals, by way of distinguishing signals characterizing the user's respiration from signals not characterizing the user's respiration. The supplementary sensing module can additionally function to provide additional data that can enrich analyses by detecting other signals from the user and/or the user's environment. The supplementary sensing module 120 preferably comprises an accelerometer, and in some variations, can additionally or alternatively comprise a gyroscope. In other variations, the supplementary sensing module 120 can further comprise a global positioning sensor (GPS) that provides location data for the user. In still other variations, the supplementary sensing module 120 can additionally or alternatively comprise additional sensors for pulse oximetry and/or electrocardiography. As such, the supplementary sensing module 120 can be configured to facilitate extraction of one or more of: the user's posture, the user's activity, the user's location, biometric signals from the user, and any other suitable signal of the user related to the user's activity, state, and/or respiration.

In variations of the supplementary sensing module 120 comprising an accelerometer, data from the accelerometer can be used to distinguish motion of the user not associated with the user's respiration characteristics from motion of the user associated with the user's respiration characteristics. For example, motion of the user associated with walking or exercising may produce signal detection at the respiration sensing module 110, and the accelerometer can be used to separate interfering data resulting from walking or exercising from data directly associated with the user's respiration characteristics. As such, the accelerometer data can be used to filter out interfering data in order to extract data relevant to the user's respiration characteristics. The accelerometer can be a single axis accelerometer, but can also be a dual- or triple-axis accelerometer. Furthermore, data from the accelerometer can function to provide enriching data associated with, for example, the user's posture (e.g., upright, laying down, slouching, sitting, etc.) and/or the user's activity (e.g., exercise, resting, sleeping, etc.).

In variations of the supplementary sensing module 120 comprising a gyroscope, data from the gyroscope can be used to distinguish motion of the user not associated with the user's respiration characteristics from motion of the user associated with the user's respiration characteristics. The gyroscope thus functions to detect orientation of the system 100, which can be used to facilitate data processing and/or can be used to enrich data for further analyses. For example, motion of the user associated with laying down or sitting upright may produce signal detection at the respiration sensing module 110, and the gyroscope can be used to separate interfering data resulting from laying down or sitting upright from data directly associated with the user's respiration characteristics. As such, the gyroscope data can be used to filter out interfering data in order to extract data relevant to the user's respiration characteristics. The gyroscope can be a single axis accelerometer, but can also be a dual- or triple-axis gyroscope. Furthermore, data from the gyroscope can function to provide enriching data associated with, for example, the user's posture (e.g., upright, laying down, slouching, sitting, etc.) and/or the user's activity (e.g., exercise, resting, sleeping, etc.).

In variations comprising a GPS, data from the GPS can be used to provide location data for the system 100 and/or the user, which can be used to enrich data detected and collected at the respiration sensing module 110. In one example, data from the GPS can indicate that the user is at a gym, and can be used to provide a label or tag for respiration signals collected while the user is at the gym. In another example, data from the GPS can indicate that the user is in a stressful environment (e.g., examination room, hospital, etc.) and can be used to provide a label or tag for respiration signals collected while the user is in the stressful environment. In yet another example, data from the GPS can indicate that the user is in a non-stressful environment (e.g., restaurant, home) and can be used to provide a label or tag for respiration signals collected while the user is in the non-stressful environment. Data from the GPS and/or other sensors of the supplementary sensing module 120 can additionally or alternatively be used to guide the user in monitoring his/her respiration behavior once the system 100 detects that the user is in any suitable environment. For example, data from the GPS can be used to guide the user's breathing behavior once the GPS and/or accelerometer has indicated that the user is exercising.

The supplementary sensing module 120 can, however, comprise any other suitable sensor or combination of sensors for providing additional data relevant to monitoring a user's respiration behavior. Furthermore, the supplementary sensing module 120 and/or any other suitable element of the system 100 can be configured to automatically or manually receive personal preference information from the user, as described in Section 2 below.

1.2 Electronics Subsystem

As shown in FIG. 1, the electronics subsystem 130 comprises a power module 131 and a signal processing module 135, and is configured to process signals of the set of signals and the supplemental set of signals. The electronics subsystem 130 can thus receive an input from at least one of the respiration sensing module 110 and the supplementary sensing module 120, and functions to process the input for further analysis in order to facilitate monitoring of the user's respiration.

The power module 131 of the electronics subsystem 130 functions to provide regulated and unregulated electrical power to the system 100 and to allow power storage for the system 100. The power module 131 preferably comprises a lithium battery that is configured to be rechargeable, but can alternatively comprise any other suitable rechargeable battery (e.g., nickel-cadmium, metal halide, nickel metal hydride, or lithium-ion polymer). Alternatively, the power module 131 can comprise a non-rechargeable battery (e.g., alkaline battery) that can be replaced to further enhance modularity in the system 100. Preferably, the power module 131 is configured to have a profile with a low aspect ratio, contributing to a thin form factor of the system 100. However, the power module 131 can be configured to have any appropriate profile such that the power module 131 provides adequate power characteristics (e.g., cycle life, charging time, discharge time, etc.) for the system 100.

In variations where the battery of the power module 131 is rechargeable, the electronics subsystem 130 can also comprise a coil of wire 132 and associated electronics that function to allow inductive coupling of power between an external power source and the power module 131, in order to enable wireless charging. The charging coil 132 preferably converts energy from an alternating electromagnetic field (e.g., provided by a charging dock), into electrical energy to charge the battery. Inductive charging provided by the charging coil 132 thus also facilitates user mobility while interacting with the system 100, such that the user can be extremely mobile while his/her respiration is being monitored. In alternative variations, however, the charging coil 132 can be altogether omitted (e.g., in variations without a rechargeable battery), or replaced or supplemented by a connection (e.g., USB connection) configured to provide wired charging of a rechargeable battery.

The signal processing module 135 of the electronics subsystem 130 is preferably coupled to the respiration sensing module 110 and the supplementary sensing module 120 and functions to condition sets of signals detected by the system 100. Outputs of the signal processing module 135 can be further processed in order to generate analyses relevant to monitoring of the user's respiration. The signal processing module 135 thus preferably comprises a microcontroller, and can additionally comprise or be coupled to any other suitable element(s), such as an amplifier, a filter, and/or an analog-to-digital converter (ADC).

In variations of the signal processing module 135 comprising a microcontroller, the microcontroller is preferably configured to control powering of the system 100, handling of signals received by the system 100, distribution of power within the system 100, and/or any other suitable function of the system 100. The control module can be configured to perform at least a portion of the method described Section 2 below, but can additionally or alternatively be configured to perform any other suitable method that facilitates respiration monitoring for a user. In some variations, the microcontroller can be preconfigured to perform a given method, with the system 100 configured such that the microcontroller cannot be reconfigured to perform a method different from or modified from the given method. However, in other variations of the system 100, the microcontroller can be reconfigurable to perform different methods.

In variations of the signal processing module 135 comprising an amplifier, the amplifier functions to amplify a signal, in order to facilitate signal processing by the system 100. The system can comprise any suitable number of amplifiers, depending upon the configuration of the amplifier(s) relative to other elements (e.g., multiplexers) of the electronics subsystem 130. In one variation, the amplifier is placed after a multiplexer in order to amplify a single output line. In another variation, a set of amplifiers is placed before a multiplexer, in order to amplify multiple input channels into the multiplexer. In yet another variation, the electronics subsystem 130 comprises amplifiers before and after a multiplexer, in order to amplify input and output lines of the multiplexer. The amplifier can also be coupled to a filter configured to suppress inter-channel switching transients (e.g., produced during multiplexing), and/or any other undesirable signals. In variations, the electronics subsystem 130 can comprise a low pass filter, a high pass filter, and/or a band pass filter configured to only allow passage of a certain range of signals, while blocking other signals (e.g., interference, noise) outside of the range of signals. The electronics subsystem 130 can additionally comprise an ADC, which functions to convert analog signals (e.g., biosignals detected by the set of sensors, amplified signals, filtered signals) into a digital quantization. The electronics system 130 can comprise any suitable number of ADCs for conversion of analog signals (e.g., from multiple channels) into digital quantizations. Furthermore, the electronics system 130 can comprise any other suitable element(s) for signal processing/conditioning.

1.3 Housing

As shown in FIG. 1, the system 100 also comprises a housing 140 configured to enclose at least a portion of the system 100. The housing 140 can also be configured to reversibly couple to elements of the system 100 (e.g., the respiration sensing module, the supplementary sensing module, and the electronics subsystem), such that the system 100 is a modular system. The housing 140 functions to protect elements of the system 100 over the lifetime usage of the system 100, and can further function to enhance wearability of the system 100. The housing 140 is preferably configured to clip to an article of a user's clothing, such that the housing can reversibly couple to the user's clothing and can be repositionable relative to the user. However, the housing 140 can additionally or alternatively be configured to couple to the user and/or the user's clothing in any other suitable manner. In one variation, the housing is integrated into an article of the user's clothing (e.g., proximal to the chest region, proximal to the abdominal region) and in an example of this variation, the housing 140 is embedded into the user's clothing (e.g., bra, waistband, belt) in a semi-permanent manner.

The housing 140 is preferably rigid; however, the housing can alternatively be flexible in order to enhance user comfort when interfacing with the system 100. To facilitate modularity, the housing 140 preferably defines or comprises a mechanism that enables reversible coupling to other elements of the system 100. In one example, the housing 140 can comprise a recess or a protrusion configured to couple to a corresponding protrusion or recess, respectively, of another element of the system 100. In another example, the housing 140 can be configured to snap-fit or press-fit with another element of the system 100 based upon mutual compliance between coupling elements. In yet another example, the housing can be configured to couple based upon friction with and/or adhesion to another element. In some variations, the housing 140 can also be configured to provide an electrical coupling with another element of the system 100. For example, the housing 140 can be configured to couple to the sensing modules 110, 120, and provide an electromechanical coupling between the sensing modules 110, 120 and the electronics subsystem 130. Furthermore the housing can also be water-resistant or waterproof, such that washing of the housing 140 does not damage the housing. As such, the housing 140 is preferably composed of a plastic material, but can alternatively be composed of any other suitable material (e.g., polymer, rubber, metal, ceramic).

In examples, as shown in FIGS. 3A-4B the housing 140 is plastic and comprises a clip 142 that is configured to couple to the user's clothing. In this example, the housing comprises a clip 142 component that is configured to reversibly couple to a unit housing the sensing modules 110, 120 and the electronics subsystem 130, such that the sensing modules 110, 120 and the electronics subsystem 130 can be replaced easily, if necessary. Furthermore, in this example, the clip 142 component is configured to electromechanically couple to the unit housing the sensing modules 110, 120 and the electronics subsystem 130, such that a data link can be coupled, through the clip component, to the electronics subsystem. In another example, multiple instances of the housing 140 are integrated into various articles of the user's clothing, wherein each housing instance is configured to reversibly couple to a unit comprising the sensing modules 110, 120 and the electronics subsystem 130. As such, the user can reversibly couple the same unit comprising the sensing modules 110, 120 and the electronics subsystem 130 to different articles of his/her clothing, in order to take advantage of system 100 modularity and to provide user convenience. The housing can, however, be configured in any other suitable manner.

1.4 System—Other Elements

As shown in FIG. 1, the system 100 can further comprise a data storage unit 150 coupled to the electronics subsystem 130, which functions to store data relevant to the respiration characteristics of the user. The data storage unit 150 can be implemented with the electronics subsystem 130, mobile device, personal computer, web browser, external server (e.g., cloud), and/or local server, or any combination of the above, in a network configured to transmit, store, and receive data. Preferably, data from the data storage unit 150 is automatically transmitted to any appropriate external device continuously; however, data from the data storage unit 150 can alternatively be transmitted intermittently (e.g. every minute, hourly, daily, or weekly).

Also shown in FIG. 1, the system 100 can further comprise a data link 160, coupled to the electronics subsystem 130 (e.g., through the housing, through a clip component), which functions to transmit an output of at least one element of the electronics subsystem 130 to a mobile device, other computing module (e.g., desktop computer, laptop computer, tablet, smartphone, health tracking device, cloud), and any suitable input to the electronics subsystem 130. Preferably, the data link 160 is a wireless interface; however, the data link 160 can alternatively be a wired connection. In a first variation, the data link 160 can include a Bluetooth module that interfaces with a second Bluetooth module included in the mobile device 161 or external element, wherein data or signals are transmitted by the data link 160 to/from the mobile device or external element over Bluetooth communications. The data link 160 of the first variation can alternatively implement other types of wireless communications, such as 3G, 4G, radio, or Wi-Fi communication. In the first variation, data and/or signals are preferably encrypted before being transmitted by the data link 160. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In a second variation, the data link 160 is a wired connection, wherein the data link includes a wired jack connector such that the electronics subsystem 130 can communicate with the mobile device and/or any external computing element through an audio jack of the mobile device and/or external computing element. In one specific example of the data link 160 that includes a wired jack, the data link 160 is configured only to transmit output signals from the electronics subsystem 130. In another specific example, the data link 160 is configured to transmit data to and from at least one element of the electronics subsystem 130 and a mobile device/external computing module (e.g., cloud). In this example, the data link 160 can transmit output signals into the mobile device through the microphone input of the audio jack of the mobile device and can retrieve data from the audio output of the audio jack of the mobile device. In this example, the data link 160 can be configured to communicate with the mobile device via inter-integrated circuit communication (I2C), one-wire, master-slave, or any other suitable communication protocol. However, the data link 160 can transmit data in any other way and can include any other type of wired connection (such as a USB wired connection) that supports data transfer between the electronics subsystem 130, the mobile device, and/or any other suitable computing element.

Figure 3A:
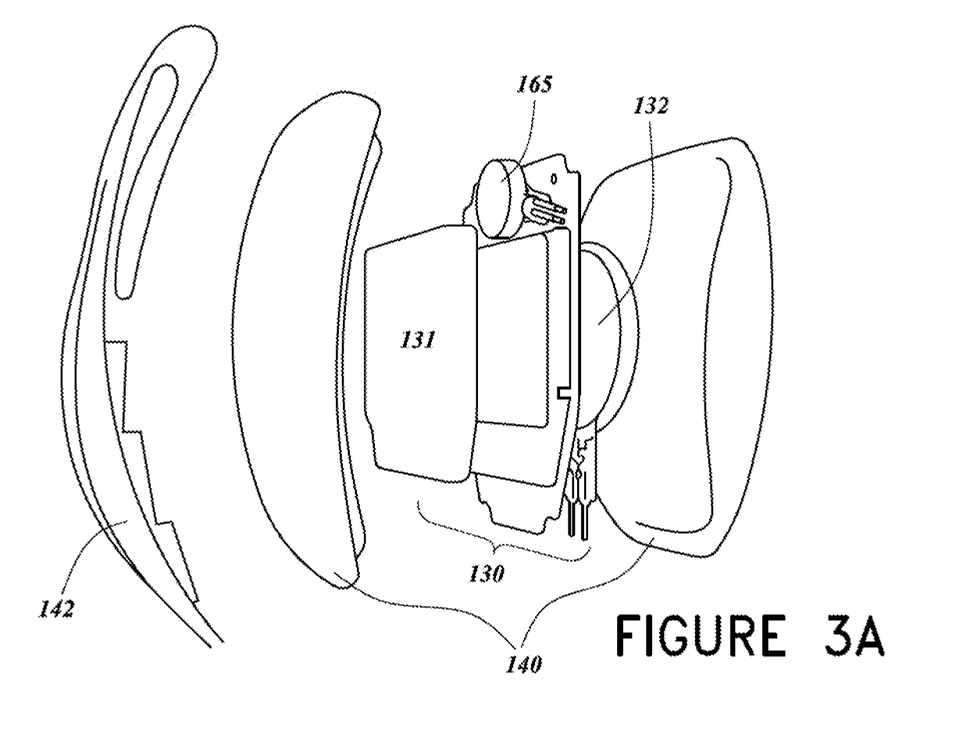
FIGS. 3A and 3B depict examples of a system for monitoring respiration of a user.
Figure 3B:
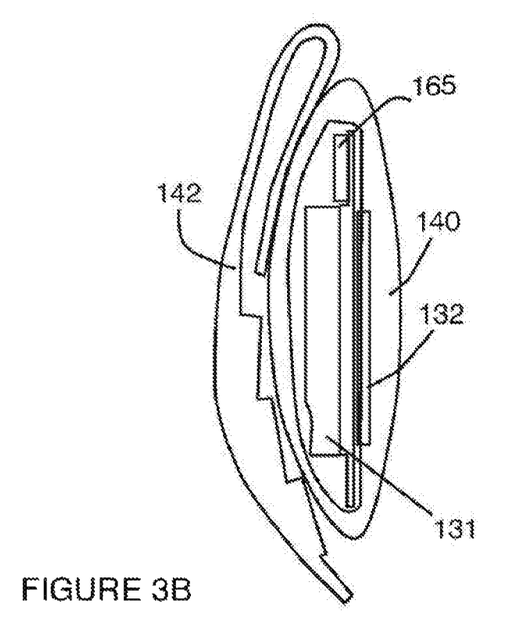
Figure 4A:
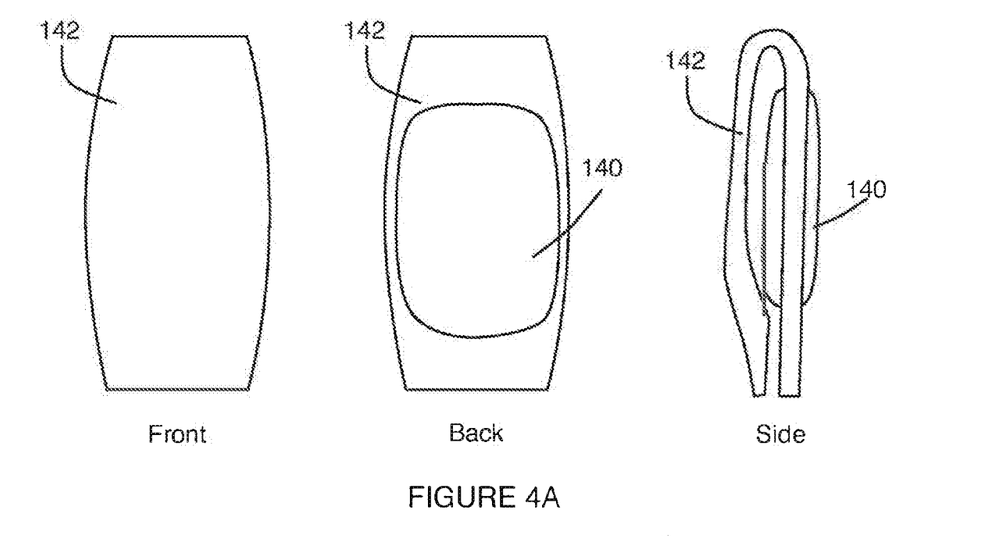
FIGS. 4A and 4B depict examples of a system for monitoring respiration of a user.
Figure 4B:
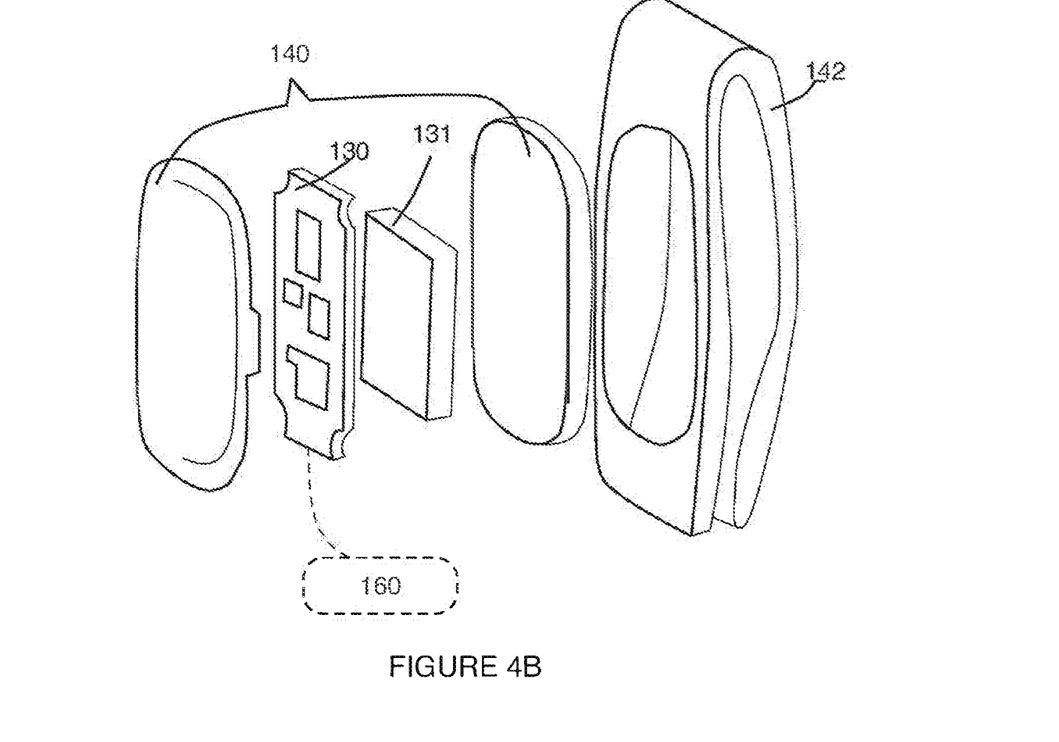

As shown in FIG. 3-A, the system 100 can also further comprise a user notification subsystem 165, which functions to provide a user notification to the user interfacing with the system 100, as described in Section 2 below. The user notification subsystem 165 is preferably coupled to the electronics subsystem 130; however, the user notification subsystem 165 can additionally or alternatively be configured relative to the system 100 in any other suitable manner. In variations, the user notification subsystem 165 is configured to provide one or more of: a haptic notification, a visual notification, an auditory notification, and any other suitable type of notification. As such, in specific examples, the user notification subsystem 165 can include one or more of: a vibration motor, as shown in FIG. 3A, a display, and a speaker.

The system 100 can also further comprise a processor 170 configured to generate an analysis based upon at least one of the set of signals received at the respiration sensing module 110, the supplementary sensing module 120, and an output of the electronics subsystem 130. In variations, the processor 170 can be configured to perform at least a portion of an embodiment of the method 200 described in Section 2 below; however, in other variations, the processor 170 can be configured to perform any other suitable method. The processor 170 can be implemented in any suitable computing module (e.g., mobile device, personal computer, cloud, etc.). The processor 170 thus functions to perform at least a portion of the method 200 described in Section 2 below, and to provide an analysis that can be used to inform the user of his/her respiration behavior in order to provide interactive respiration monitoring for the user. During generation of the analysis, the processor 170 can be configured to associate respiration events (e.g., coughing, laughing, wheezing, apnea, sighing) and/or other user events (e.g., user activities) captured in the set of signals, based upon data from the sensor(s) of the respiration sensing module 110 and/or the supplementary sensing module (e.g., accelerometer, gyroscope, GPS). The analysis can comprise a generated metric that generally informs the user of his/her respiration behavior quality, in relation to respiration events and/or user events, and can additionally or alternatively comprise metric(s) that quantify respiration characteristics (e.g., rate, flow parameters, inhalation-to-exhalation ratio, etc.) of the user in relation to respiration events and/or user events. Based upon the generated analysis, the processor 170 can also be configured to provide a user notification (e.g., recommendation) to the user that affects his/her respiration behavior, such that the processor facilitates a change in the user's respiration behavior. As such, at least one of the analysis, metric(s), and recommendation can be provided to the user at a user interface in any suitable manner (e.g., audibly, visually, haptically). Thus, in examples, an output of the processor 170 can be used to provide a notification to the user by way of at least one of a speaker, a visual display, and a vibration motor, as described above. In one such example, the notification can be provided to the user at a mobile device of the user. The processor 170 can, however, be configured to provide feedback to the user in any other suitable manner. Furthermore, variations of the processor 170 can be configured to implement a machine learning algorithm (e.g., supervised, unsupervised) configured to identify respiration signatures of the user, such that analysis of the set of respiration signals improves with the quantity of respiration data acquired from the user. In some variations, the machine learning algorithm can also be trained with a set of exemplary data configured to provide a base set of features configured to train the algorithm to distinguish certain base traits from the respiration waveform. Furthermore, the algorithm can be adapted to a respiration signals from a single user, and/or signals from multiple users.

As a person skilled in the field of biosignal monitoring devices will recognize from the previous detailed description and from the figures and claims, modifications and changes can be made to the embodiments, variations, examples, and specific applications of the system 100 described above without departing from the scope of the system 100.

2. Method

Figure 5:
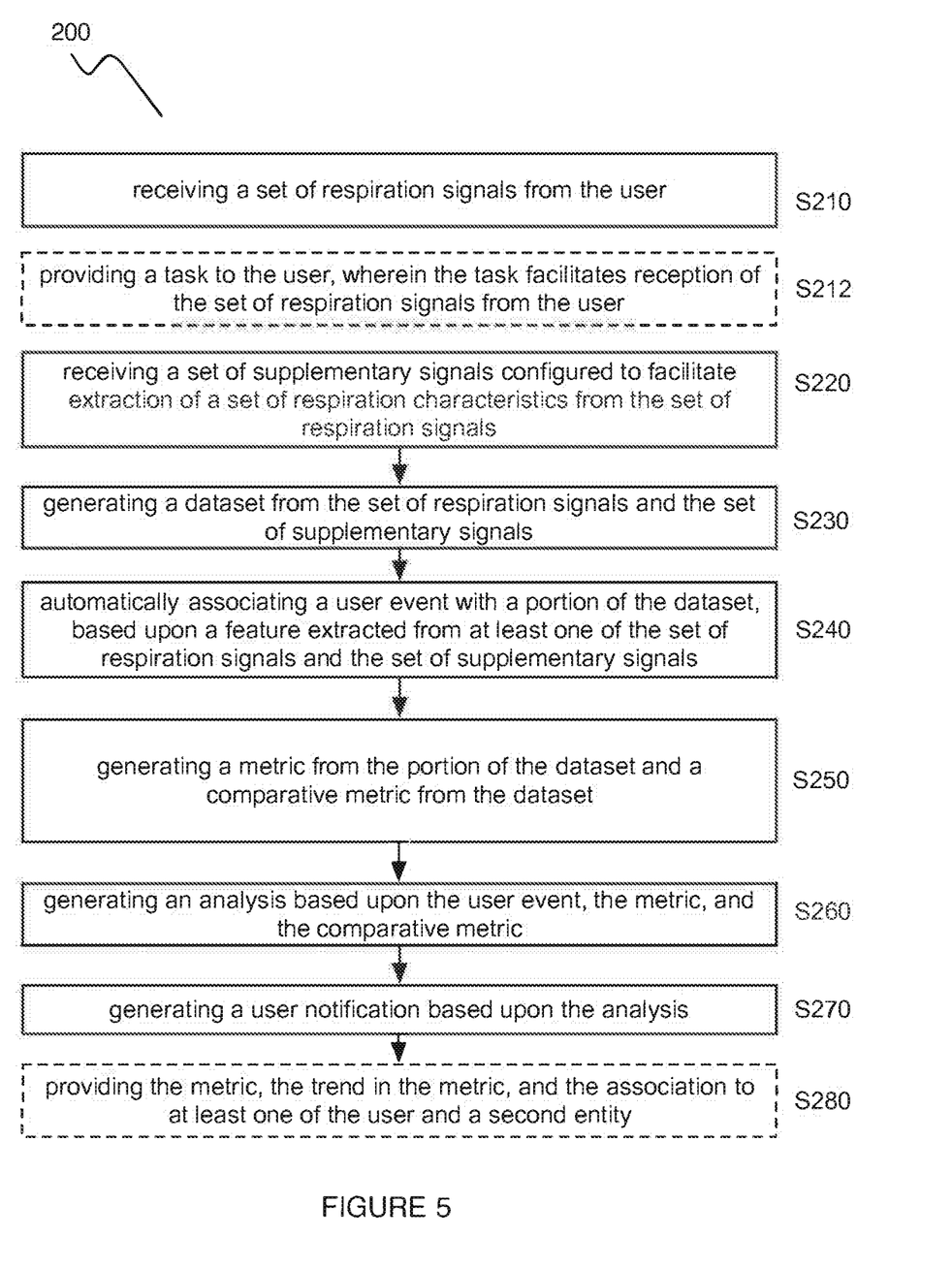
FIG. 5 depicts an embodiment of a method for monitoring respiration of a user.
Figure 6A:
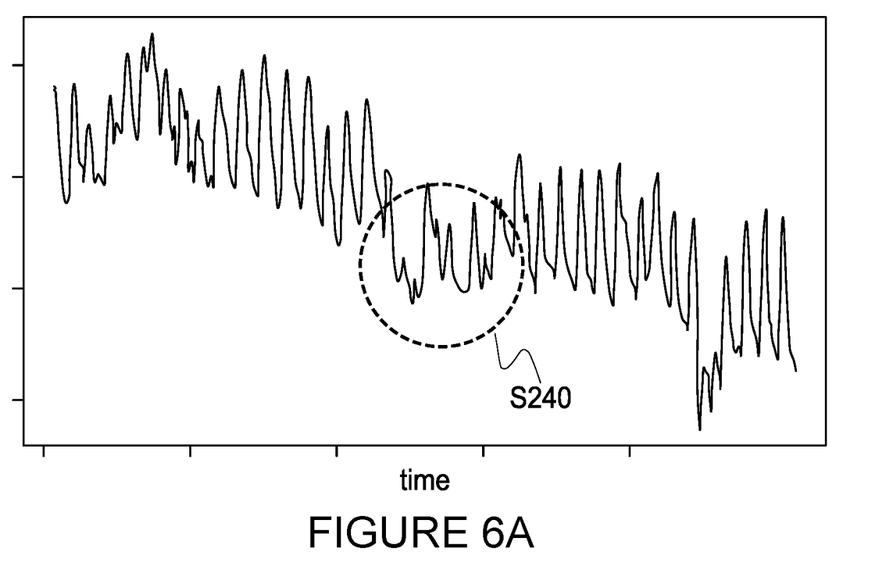
FIGS. 6A-6D depict example outputs of an embodiment of a method for monitoring respiration of a user.
Figure 6B:
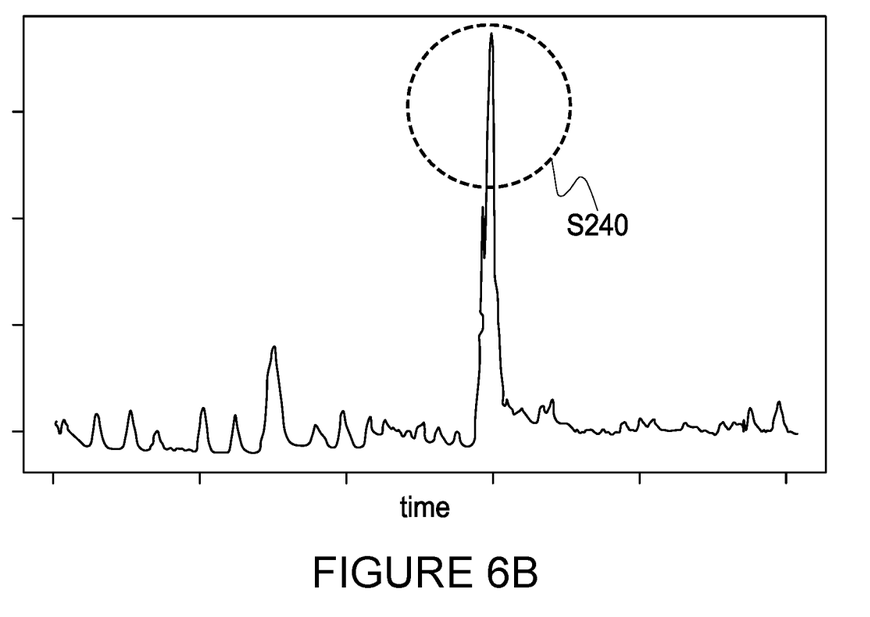
Figure 6C:
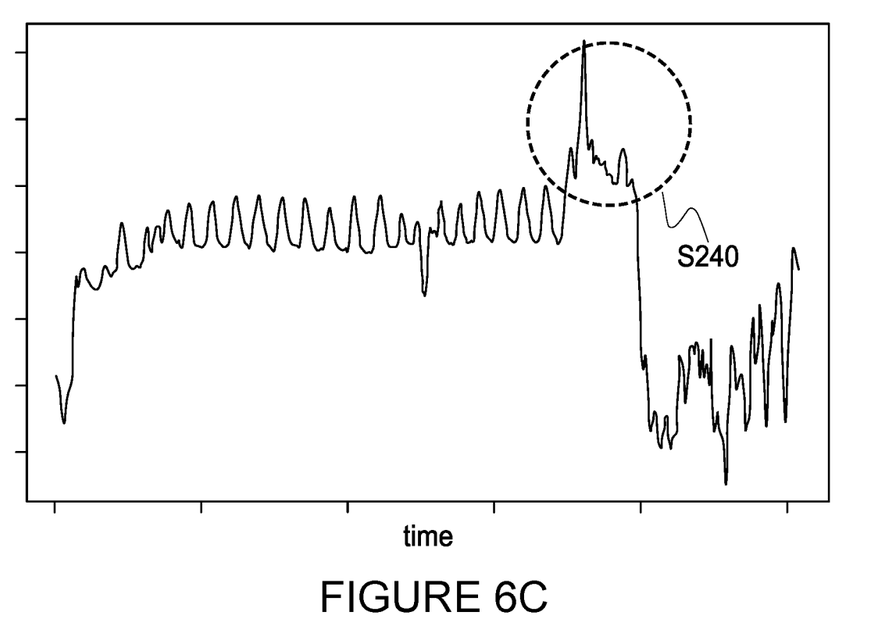
Figure 6D:
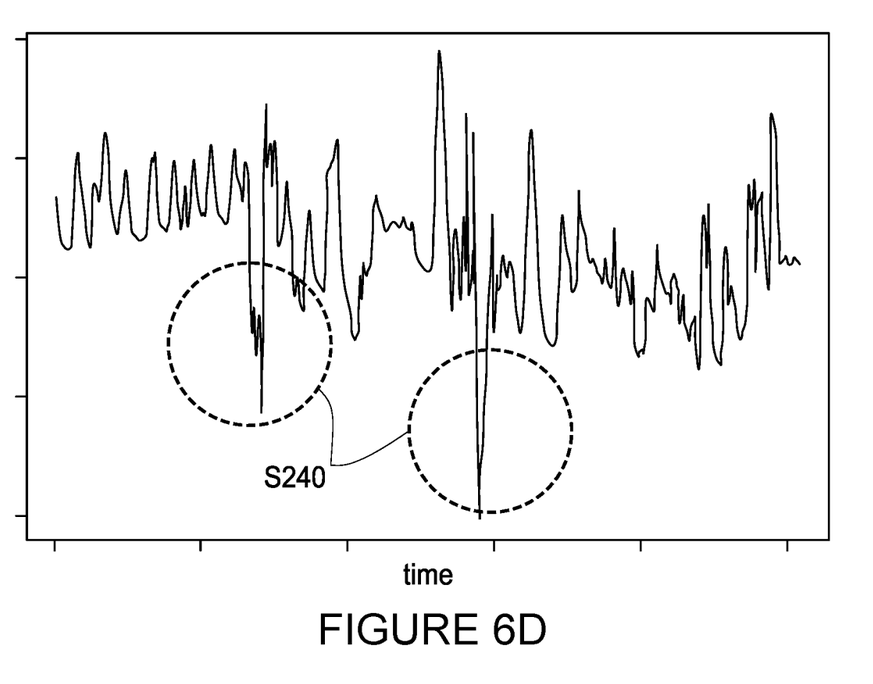

As shown in FIG. 5, an embodiment of a method 200 for monitoring respiration of a user comprises: receiving a set of respiration signals from the user S210; receiving a set of supplementary signals configured to facilitate extraction of a set of respiration characteristics from the set of signals S220; generating a dataset from the set of signals and the set of supplementary signals S230; automatically associating a user event with a portion of the dataset, based upon a feature extracted from at least one of the set of respiration signals and the set of supplementary signals S240; generating a metric from the portion of the dataset and a comparative metric from the dataset S250; generating an analysis based upon the user event, the metric, and the comparative metric S260; and providing a user notification to the user based upon the analysis S270. The method 200 can further comprise providing the metric, the trend in the metric, and the association to at least one of the user and a second entity S280, which can enable a second entity to facilitate monitoring of the user's respiration behavior. The method 200 can be used to facilitate monitoring of the respiration of the user, and can further function to assist the user in modifying his or her behavior to adjust his/her respiration behavior in a beneficial way.

Block S210 recites: receiving a set of respiration signals from the user, and functions to receive a set of signals from the user, in order to generate respiration data and/or metrics that can be used to monitor the user's respiration. Block S210 is preferably implemented using an embodiment of the system 100 described in Section 1 above, and more, specifically, using a variation of the respiration sensing module described above; however, Block S210 can be implemented using any suitable sensor system configured to detect respiration signals from a user. The set of respiration signals in Block S210 is preferably received and transmitted continuously and substantially in real time; however, the set of signals can alternatively be received and transmitted non-continuously and/or in non-real time. Preferably, the set of respiration signals is received within a time window (e.g. a minute time window, an hour time window, a 24-hour time window) spanning a set of time points, such that the user's respiration behavior can be monitored over the time window in order to link an analysis generated from the set of signals to a time window that is relevant to the user.

In some variations, Block S210 can include providing a task to the user S212, wherein the task facilitates provision and/or reception of the set of respiration signals from the user. In one variation, the task can be provided by way of an application executing on a computing device of the user (e.g., mobile device, tablet, personal computer, etc.), wherein the computing device is coupleable to an embodiment of a system that receives the set of set of respiration signals. Additionally, provision of the task is preferably performed substantially concurrently with reception of the set of respiration signals, such that the set of respiration signals and the task are substantially synchronized. However, the task can be provided in any other suitable manner, using any other suitable system, and/or without temporal synchronization.

The task preferably enables the user to modulate his/her respiratory state, which can indirectly and/or directly affect any other suitable neurocognitive and/or physiological state of the user. In variations, the task can function to affect any one or more of: the user's focus, the user's attention, the user's mental stress level, the user's physiological stress level, the user's fatigue, the user's balance, the user's cardiovascular health, the user's respiratory health, and any other suitable neurocognitive and/or physiological state of the user. In one example, the task can be provided in the form of a game executing on a mobile device of the user, wherein the game assists the user in achieving a desired and/or beneficial respiration state. In the example, the game can thus provide feedback to the user, in order to modulate a respiration state of the user. In specific examples, the game can instruct the user to maintain a position of an animated object (e.g., a feather, a pendulum, a teeter-totter) rendered at a display of the mobile device, wherein the user maintains the position of the animated object by adjusting a respiration parameter (e.g., rate of respiration, respiration waveform profile, etc.). A user's performance of the task can thus be determined based upon a duration over which the user maintains a desired respiration state, a variance metric (e.g., standard deviation, variance) characterizing variations in the user's respiration state, a sociocomparative metric characterizing the user's performance of the task relative to past performances by the user and/or to one or more additional users, and/or any other suitable performance metric.

Block S220 recites: receiving a set of supplementary signals configured to facilitate extraction of a set of respiration characteristics from the set of respiration signals, and functions to provide additional data that facilitates processing of the set of respiration signals indicative of the set of respiration characteristics. Block S220 can enable distinguishing of signals characterizing the user's respiration from signals not characterizing the user's respiration and can provide additional data that can enrich analyses by taking into account other data from the user and/or the user's environment. Block S220 can additionally or alternatively enable generation and/or provision of notifications to the user, as described below with respect to Block S270. Block S220 is preferably implemented using an embodiment of the system 100 described in Section 1 above, and more, specifically, using a variation of the supplementary sensing module comprising at least one of an accelerometer, a gyroscope, and a GPS described above; however, Block S220 can be implemented using any suitable sensor system configured to detect supplementary signals from a user. Similar to Block S210, the set of supplementary signals in Block S220 is preferably received and transmitted continuously and substantially in real time; however, the set of supplementary signals can alternatively be received and transmitted non-continuously and/or in non-real time. Furthermore, the set of supplementary signals can be received automatically, and/or manually (e.g., upon user input, upon input by another entity). Preferably, the set of supplementary signals is also received within a time window (e.g. a minute time window, an hour time window, a 24-hour time window) spanning a set of time points.

In one variation, the set of supplementary signals can be provided, at least in part, by the user providing the set of respiration signals. In this variation, the set of supplementary signals can include information provided by the user, wherein the information indicates personal preferences of the user, with regard to performing activities that can affect a respiration, neurocognitive, and/or other physiological state of the user. In one example, the information provided by the user can include any one or more of: dietary preferences (e.g., favorite foods, favorite restaurants, food allergies, etc.), exercise preferences (e.g., favorite gym locations, favorite types of exercise), activity preferences to reduce stress (e.g., reading, watching movies, socializing, etc.), and any other suitable preference of the user. The information contributing to the set of supplementary signals can then be used, for instance, to provide personalized notifications to the user (e.g., in Block S270), and/or for any other suitable purpose to affect the user's respiration. In this variation, the information can be retrieved manually, for instance, based upon input provided by the user and/or another entity associated with the user at an input module (e.g., keyboard, keypad, touchscreen, voice detection module, etc.). Additionally or alternatively, the information can be retrieved automatically, for instance, based upon accessing of the user's social networks for status updates, location check-ins, reviews of vendors, reviews of service providers, and any other suitable social network. Additionally or alternatively, the information can be retrieved automatically using sensors configured to detect one or more of: the user's food/beverage consumption (e.g., spectophotometers), the user's activity level (e.g., accelerometers, gyroscopes), the user's location (e.g., GPS elements), and/or any other suitable sensor.

In some variations, the set of supplementary signals received in Block S220 can be used to distinguish motion of the user not associated with the user's respiration characteristics from motion of the user associated with the user's respiration characteristics, based upon accelerometer and/or gyroscope signals. For example, motion of the user associated with laying down or sitting upright may produce signal detection at a respiration sensing module in an example of Block S210, and signals from a supplementary sensing module used in Block S220 can be used to separate interfering signals resulting from laying down or sitting upright from data directly associated with the user's respiration characteristics. Additionally or alternatively, in some variations, the set of supplementary signals can be used to enrich the set of data generated in Block S230. In one example, signals from a GPS of a supplementary sensing module can indicate that the user is at a gym, and can be used to provide a label or tag for respiration signals collected while the user is at the gym. In another example, signals from an accelerometer of a supplementary sensing module can indicate that the user is running, and can be used to provide a label or tag for respiration signals collected while the user is running. In yet another example, signals from a gyroscope of a supplementary sensing module can indicate that the user is lying down, and can be used to provide a label or tag for respiration signals collected while the user is resting. As such, supplementary signals can be used to additionally or alternatively identify activities and/or events of the user, that can be associated with data generated from the set of respiration signals and/or the set of supplementary signals.

The set of respiration characteristics characterized in the set of respiration signals and extracted using the set of supplementary signals preferably comprises any one or more of: respiration rate (e.g., breaths per second), depth of breath, shallowness of breath, inhalation-to-exhalation ratio, thoracic variations, tidal volume (or an estimation thereof), inspiratory flow (e.g., peak value, mean value), expiratory flow (e.g., peak value, mean value), fractional inspiratory time, work of breathing, phase angle, respiration waveform morphology (e.g., shape, area under waveform, regularity of waveform, etc.), any other suitable respiration characteristic, and any other suitable derivative of a respiration characteristic. With regard to respiration waveform morphology, Block S210 and/or Block S220 can enable characterization of respiration characteristics, including, for example, a sharpness of a transition between inhalation and exhalation for a user, as indicated by the respiration waveform, a length of breath holding by the user, as indicated by the respiration waveform, or any other suitable factor. Additionally, the set of respiration characteristics received can indicate respiration events associated with laughter, sighing, wheezing, coughing, apnea, and/or any other suitable event associated with the user's respiration. In some variations, extraction of the set of respiration characteristics can include implementing a machine learning algorithm (e.g., supervised, unsupervised) configured to identify respiration signatures of the user, such that analysis of the set of respiration signals improves with the quantity of respiration data acquired from the user. In some variations, the machine learning algorithm can also be trained with a set of exemplary data configured to provide a base set of features configured to train the algorithm to distinguish certain base traits from the respiration waveform. Furthermore, the algorithm can be adapted to a respiration signals from a single user, and/or signals from multiple users.

Block S230 recites: generating a dataset derived from the set of respiration signals and the set of supplementary signals, and functions to convert signals received in Blocks S210 and S220 into a set of quantitative data for determining a metric characterizing the user's respiration. Preferably, Block S230 includes transforming an electrical signal (e.g., resistance, voltage, impedance, or capacitance), produced by an embodiment of a sensing module described above, into a set of quantitative parameters. Preferably, the set of quantitative parameters is generated at time points within a given time window (e.g., during which respiration and/or supplementary signals are received), in order to facilitate generation of a trend in a metric, based upon at least one respiration characteristic of the set of respiration characteristics characterizing the user's respiration. Also, the dataset preferably includes data from which absolute values and changes in value of at least respiration characteristic of the set of respiration characteristics can be extracted. In an example, for each time point of a time window for signal collection, the dataset captures a value of respiration rate (e.g., breaths per second), depth of breath, shallowness of breath, inhalation-to-exhalation ratio, thoracic variations, tidal volume (or an estimation thereof), inspiratory flow, expiratory flow, work of breathing, phase angle, respiration waveform morphology (e.g., shape, area under waveform, regularity of waveform, etc.), any other suitable respiration characteristic, and any other suitable derivative of a respiration characteristic. Additionally, the dataset can include qualitative data, such as qualifiers characterizing desired ranges of values for a given respiration characteristic (e.g., within target range, below target range, above target range).

Block S240 recites: automatically associating a user event with a portion of the dataset, based upon a feature extracted from at least one of the set of respiration signals and the set of supplementary signals, and functions to identify and tag a user event within the dataset. As such, Block S240 can associate user events (e.g., activities, respiration events)

with portions of the dataset characterizing at least one respiration characteristic of the set of respiration characteristics. The user event can define a user activity (e.g., exercise, rest, sleep) from supplementary signal data, a user orientation (e.g., slouching, sitting, laying down) from supplementary signal data, a user location from supplementary signal data, and/or a user respiration event (e.g., apnea, laughing, coughing, wheezing) from respiration signal data and/or supplementary signal data. The user event can additionally or alternatively be derived from accessing electronic information of the user, including information accessible by social networks of the user. For instance, status updates, check-ins, and/or any other suitable information, derived from social networks of the user, can be used to determine the user event(s). As such, characteristic events identified from the respiration signals and/or the supplementary signals can be automatically tagged in the dataset in order to create unique signatures for user events. As shown in FIGS. 6A-6D, the user event can comprise a signal feature that is identifiable within the set of data, based upon signal pattern, signal amplitude, signal frequency, signal repetition, signal uniformity, etc. In examples shown in FIGS. 6A-6D, signal features associated with talking, laughing, and coughing can be identified as respiration events that are associated with portions of the set of data. In other examples, features from accelerometer and/or gyroscope data can be used to identify and associate user activities with portions of the dataset. Block S240 can further comprise associating a condition of the user's environment (e.g., location, temperature, etc.), derived from the set of supplementary signals, with a portion of the dataset and/or the user event, in order to enrich analyses based upon the dataset. Block S240 is preferably implemented using an embodiment of the system 100 described in Section 1 above, and specifically, using a variation of the processor described above. However, Block S240 can alternatively be implemented using any other suitable processing element.

Block S250 recites: generating a metric from the portion of the dataset and a comparative metric based upon the set of data, and functions to generate metrics and/or trends in metrics based upon the set of respiration signals received, the set of supplementary signals received, and any associated respiration events identified within the dataset. Preferably, the metric is determined based upon an algorithm incorporating multiple respiration characteristics captured within the set of respiration signals received in Block S210, such that the metric is a comprehensive metric characterizing an overall state of a user's respiration state. However, generating a metric in Block S250 can additionally or alternatively comprise generating a metric characterizing a single respiration characteristic (e.g., respiration rate, flow parameter) captured within the set of signals received in Block S210. The metric is preferably generated in a manner that incorporates one or more time points of data relevant to a user event identified in Block S240, such that the metric characterizes the portion of the dataset associated with the user event.

Preferably, the comparative metric is a trend in the metric determined for the portion of the dataset associated with the user event, wherein the trend in the metric is generated over a time window or subset of a time window during which signals are collected. The time window can include times associated with the user event or can omit times associated with the user event. Furthermore, the time window is preferably longer in duration than the duration of the user event, but can alternatively be shorter or equal in duration to the duration of the user event. In one example, the comparative metric can include a graph that plots the metric over a set of time points spanning the time window; however, the trend in the metric may alternatively be any appropriate visual that displays a variation in the metric or time or over any other suitable parameter. In one variation, the comparative metric can include an average metric, calculated over a time window or subset of a time window during which signals are collected, which can facilitate comparisons between a metric associated with a user event, and a comparative (e.g., average metric) associated with other portions of the dataset. In yet another variation the comparative metric can include a metric determined for at least one other occurrence of the user event. In still another variation, the comparative metric can be derived from signals collected from at least one other user, in order to facilitate comparisons between users of the same or different demographics.

In some variations of Block S250, the metric can be derived from the user's performance on the task provided in Block S212, such that the metric is not directly calculated from the user's respiration, but alternatively is calculated from the user's performance of a task indirectly related to the user's respiration. In examples, the metric can characterize a duration over which the user maintained a desired respiration state while performing the task, a variance metric (e.g., standard deviation, variance) characterizing variations in the user's respiration state while performing the task, a sociocomparative metric characterizing the user's performance of the task relative to past performances by the user and/or to one or more additional users, and/or any other suitable performance metric.

Block S260 recites: generating an analysis based upon the user event, the metric, and the trend in the metric, and functions to facilitate associations between user events and metrics of the user's respiration characteristic(s), in a manner that is meaningful to a user. Preferably, the user event is associated with metrics determined at time points spanning the user event, such that direct associations can be made between user events and metrics (e.g., a metric associated with the user event and a comparative metric) over time. In one example, a metric that quantifies the user's breathing efficiency, based upon multiple characteristics, can be associated with a user exercise event, such that the breathing efficiency metric describes the user's breathing efficiency at time points spanning a user's exercise session. In another example, a metric that quantifies the user's breathing depth can be associated with a stressful user event (e.g., exam period), such that the breathing depth metric describes the user's breathing depth at time points spanning a user's exam period. In another example, a graph of a metric (e.g., respiration depth vs. time or comprehensive respiration metric vs. time) is copresented with indicators of user events (e.g., sleep periods, stress periods).

In one variation, the analysis can compare a metric associated with a user event with a comparative metric not associated with the user event, such that the analysis provides insight into differences and/or similarities between respiration characteristics for different user states. In one example, the analysis can provide insight into respiration characteristics of the user while the user is experiencing stress (i.e., the user event) and while the user is not experiencing stress, such that the analysis can inform the user of respiration behaviors that are associated with the user's stress. In another example, the analysis can provide insight into respiration characteristics of the user while the user is performing a task well and while the user is not performing a task well, such that the analysis can inform the user of respiration behaviors that are associated with competency in performing a task.

In another variation, the analysis can compare a metric associated with a user event, with a comparative metric determined for another occurrence of the user event, such that the analysis facilitates determination respiration behavior changes in relation to repeat performances of the same user event. In an example, the analysis can provide insight into the user's respiration behavior associated with running over time, such that the user can improve his/her breathing behavior during running, based on the analysis. In another example, the analysis can provide insight into the user's respiration behavior associated with stress over time, such that the user can track his/her breathing behavior during periods of stress, based upon the analysis.

Block S270 recites providing a user notification to the user based upon the analysis, and functions to provide a mechanism to promote change in user respiration behaviors. The user notification preferably contains information relevant to a "respiration status" of the user, and can be associated with a user event or an anticipated occurrence of a user event. In some variations, the user notification can indicate a rising, decreasing, or steady level of a metric, and/or a metric that is within or out of a desired range. The user notification is preferably provided in substantially real time (e.g., within 3 breathing cycles), but in some variations, can be provided in non-real time. Furthermore, the user notification(s) can be provided continuously, but in some variations, can be provided non-continuously. Furthermore, data from sensors (e.g., of a supplementary sensing module) can additionally or alternatively be used to generate user notifications that guide the user in monitoring his/her respiration behavior once sensors indicate that the user is in a specific environment. For example, data from a GPS and an accelerometer can be used to generate a user notification that guides the user's breathing behavior once the GPS and/or accelerometer has indicated that the user is exercising within a gym environment. The user notification can be provided to the user by way of a messaging client configured to transmit a message to the user, and in examples, can include a text messaging client, an in-application messaging client, an email client, and any other suitable messaging client. In other examples, the user notification can be provided to the user in any other suitable manner (e.g., visually rendered, provided in an auditory manner, provided in a tactile/haptic manner, etc.). As such, in one application, the user notification can be provided in substantially real time (e.g., within three breathing cycles) at a haptic module (e.g., a module comprising a vibration motor) of a respiration monitoring system worn by the user. The user notification can be provided by way of a computing device (e.g., mobile device, tablet, personal computer, etc.) coupled to or in communication with an embodiment of the system 100 described above; however, the user notification can be provided using any other suitable device or element. In one example, the user notification can indicate that a respiration depth of the user is decreasing upon entering a stressful experience, such that the user can adjust his/her breathing behavior to cope with the stressful experience. In another example, the user notification can indicate that the user has been in a stressed state, as indicated in the user's respiration, for a given duration of time. In another example, the user notification can indicate that the user's breathing is not efficient (e.g., based upon a breathing efficiency metric) during exercise, such that the user is able to adjust his/her breathing according to the notification. In some variations, the user notification can additionally include an explicit directive for the user to perform a certain action (e.g., breathe deeper, breathe shallower, adjust posture, etc.) that affects the user's respiration positively. Therefore, the user notification preferably systematically and repeatedly facilitates analysis of a respiration status of the user based upon at least one metric of the user and provides and alert and/or advice to facilitate management and monitoring of a user's respiration substantially in real time.

In some variations of the method 200, wherein the user provides his/her personal preferences in the set of supplementary signals, the user notification provided in Block S270 can be a personalized notification to perform an activity that affects the user's respiration/neurocognitive/physiological state based upon the user's personal preferences. For example, Block S270 can include providing a notification that the user performs a physical activity that he/she prefers, in order to reduce a state of stress, as indicated in the analysis determined in Block S260. In a specific example, if the user has an affinity toward dancing, and is determined to be in a state of stress that can be improved by physical activity, the user notification provided in Block S270 can recommend that the user take a dancing class at a local gym, or go to a dancing club with acquaintances of the user. In other variations of the example, however, the user notification can recommend any other suitable activity to the user based upon the user's personal preferences.

As shown in FIG. 5, the method 200 can further comprise Block S280, which recites: providing the metric, the trend in the metric, and the association to at least one of the user and a second entity. Block S280 functions to facilitate monitoring of the user's respiration by the second entity. The second entity is preferably a caregiver of the user, such as a parent, family member, health coach, personal trainer, teacher, supervisor, boss, or health care professional servicing the user; however, the second entity can alternatively be any entity (e.g., a human, a processing element) monitoring the user's respiration. Preferably, the second entity has access to all analyses provided to the user, as well as user notifications provided to the user. Additionally, the second entity can have access to analyses and/or notifications for multiple users. In an example, a personal trainer can have access to analyses an/or notifications for his or her trainees, such that the personal trainer can monitor the respiration of multiple patients simultaneously.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 135 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A wearable respiration monitor, comprising:
   a housing, having a first side and an opposing second side, the housing configured to be attached to an article of clothing of a wearer, the housing comprising an exterior surface and an interior volume formed by the exterior surface;
   a first coupling on the second side, configured to attach to an inside surface of the article of clothing to support the housing in between the clothing and the wearer; and
   a capacitive sensor enclosed within the housing, to detect force exerted against the housing by a body of the wearer as a result of respiratory patterns of the wearer;
   the capacitive sensor comprising first and second conductive plates positioned in the interior volume of the housing and configured to not come into direct contact with the body of the wearer when the housing is attached to the article of clothing of the wearer, the first and second conductive plates being further configured to produce an electrical signal indicative of the respiratory patterns of the wearer in response to deflection of the first conductive plate relative to the second conductive plate responsive to the force exerted against the housing by the body of the wearer.

2. A wearable respiration monitor as in claim 1, further comprising a pulse oximetry sensor.

3. A wearable respiration monitor as in claim 1, further comprising a photoplethysmography sensor.

4. A wearable respiration monitor as in claim 3, further comprising a 3-axis accelerometer.

5. A wearable respiration monitor as in claim 1, further comprising a data storage unit configured to store data relevant to respiration characteristics of the wearer.

6. A wearable respiration monitor as in claim 5, further comprising a processor configured to generate an analysis based upon the respiration characteristics of the wearer.

7. A wearable respiration monitor as in claim 1, wherein the capacitive sensor exhibits a change in capacitance in response to compression caused by the force exerted against the housing by the body of the wearer.

8. A wearable respiration monitor as in claim 1, further comprising a gyroscope.

9. A wearable respiration monitor as in claim 1, further comprising a global positioning sensor.

10. A wearable respiration monitor as in claim 1, further comprising a processor.

11. A wearable respiration monitor as in claim 1, wherein the first side provides a substantially single point of contact with the wearer.

12. A wearable respiration monitor as in claim 11, wherein the capacitive sensor detects the force exerted against the housing by the body of the wearer in a direction perpendicular to the first side of the housing.

13. A wearable respiration monitor as in claim 12, wherein the capacitive sensor exhibits a change in capacitance in response to the application of the force exerted by the body of the wearer to the first side of the housing.

14. A wearable respiration monitor as in claim 1, wherein the housing is configured such that an adhesive layer is attachable to an undergarment such that it can hold the first side against the wearer's body.

15. A wearable respiration monitor as in claim 1, wherein the first and second conductive plates of the capacitive sensor are parallel, spaced apart, and separated by a non-rigid material.

16. A wearable respiration monitor as in claim 1, wherein the housing is flexible to enhance wearer comfort.

17. A wearable respiration monitor as in claim 16, wherein the housing is waterproof.

18. A wearable respiration monitor as in claim 1, further comprising a wireless data link.

19. A wearable respiration monitor as in claim 1, wherein the first coupling comprises an adhesive.

20. A wearable respiration monitor as in claim 1, wherein the first coupling comprises a clip.

21. A wearable respiration monitor as in claim 1, wherein the first coupling comprises a strap.

* * * * *

UNITED STATES PATENT AND TRADEMARK OFFICE
CERTIFICATE OF CORRECTION

PATENT NO. : 11,039,788 B2
APPLICATION NO. : 16/271492
DATED : June 22, 2021
INVENTOR(S) : Jonathan Paul K. Palley Page 1 of 1

It is certified that error appears in the above-identified patent and that said Letters Patent is hereby corrected as shown below:

In the Specification

In Column 1, Line 12 (Approx.), delete "entirety" and insert --entirety.--.

In Column 1, Line 61, delete "I." and insert --1.--.

In Column 12, Line 6, delete "3-A," and insert --3A,--.

In Column 15, Line 30, delete "spectophotometers" and insert --spectrophotometers--.

In Column 20, Line 44, delete "an/or" and insert --and/or--.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*